(12) United States Patent
Walker et al.

(10) Patent No.: US 6,887,244 B1
(45) Date of Patent: May 3, 2005

(54) CORDLESS SURGICAL HANDPIECE WITH DISPOSABLE BATTERY; AND METHOD

(75) Inventors: Douglas W. Walker, Ventura, CA (US); Frank M. Ordaz, Ventura, CA (US); M. Terry Olson, Ventura, CA (US)

(73) Assignee: Medtronic, Inc., Minneapolis, MN (US)

( * ) Notice: Subject to any disclaimer, the term of this patent is extended or adjusted under 35 U.S.C. 154(b) by 585 days.

(21) Appl. No.: 09/668,831

(22) Filed: Sep. 22, 2000

Related U.S. Application Data

(63) Continuation of application No. 09/349,643, filed on Jul. 8, 1999, now Pat. No. 6,126,670.

(60) Provisional application No. 60/112,678, filed on Dec. 16, 1998.

(51) Int. Cl.[7] .............................................. A61B 17/16
(52) U.S. Cl. ....................................................... 606/80
(58) Field of Search ............................ 606/1; 429/123, 429/99; 173/217; 206/704, 705, 703; 607/151; 439/21, 22, 176, 312, 322, 909

(56) References Cited

U.S. PATENT DOCUMENTS

| | | | |
|---|---|---|---|
| 2,469,857 A * | 5/1949 | Allyn .......................... 439/334 |
| 2,986,612 A * | 5/1961 | Healy ........................ 200/51 R |
| 3,184,703 A * | 5/1965 | Piscitello et al. ............ 439/335 |
| 3,550,280 A * | 12/1970 | Palm ........................... 30/217 |
| 3,734,207 A * | 5/1973 | Fishbein ...................... 173/217 |
| 4,032,806 A * | 6/1977 | Seely .......................... 310/50 |
| 4,728,876 A | 3/1988 | Mongeon et al. |
| 4,751,452 A * | 6/1988 | Kilmer et al. ................ 310/50 |
| 4,823,244 A * | 4/1989 | Alaybayoglu et al. ....... 362/194 |
| 5,207,697 A * | 5/1993 | Carusillo et al. ........... 606/167 |
| 5,259,116 A * | 11/1993 | Laube .......................... 30/216 |
| 5,368,954 A * | 11/1994 | Bruns ......................... 429/123 |
| 5,489,484 A * | 2/1996 | Wheeler et al. ............. 429/123 |
| 5,499,985 A | 3/1996 | Hein et al. |
| 5,553,675 A * | 9/1996 | Pitzen et al. ................. 173/217 |
| 5,643,297 A * | 7/1997 | Nordgren et al. ............. 604/22 |
| 5,796,188 A | 8/1998 | Bays |
| 5,843,132 A | 12/1998 | Ilvento |
| 6,112,414 A * | 9/2000 | Andis et al. ................... 30/231 |
| 6,126,670 A * | 10/2000 | Walker et al. ............... 173/217 |
| 6,139,359 A * | 10/2000 | Fuhreck et al. ............. 439/349 |

FOREIGN PATENT DOCUMENTS

EP          0 817 300 A3     12/1998

* cited by examiner

*Primary Examiner*—David O. Reip
*Assistant Examiner*—D. Jacob Davis
(74) *Attorney, Agent, or Firm*—Haynes and Boone, LLP

(57) ABSTRACT

A surgical procedure is disclosed utilizing a cordless surgical handpiece powered from a sterile battery pack that contains a battery in condition for immediate use without further charging or sterilization. The battery chemistry is based upon lithium/manganese dioxide, and the battery after a single use may be disposed of into non-hazardous waste. The compact surgical handpiece has a brushless DC motor and a manually operated external trigger for activating and controlling the motor operations. Interengaging sets of contacts on the handpiece and battery are adapted to become lockingly and conductively interengaged upon rotation of the battery pack relative to the handpiece, in a manner that rapidly achieves correct alignment of the parts and also ensures stable mechanical attachment and support during the surgical procedure.

16 Claims, 7 Drawing Sheets

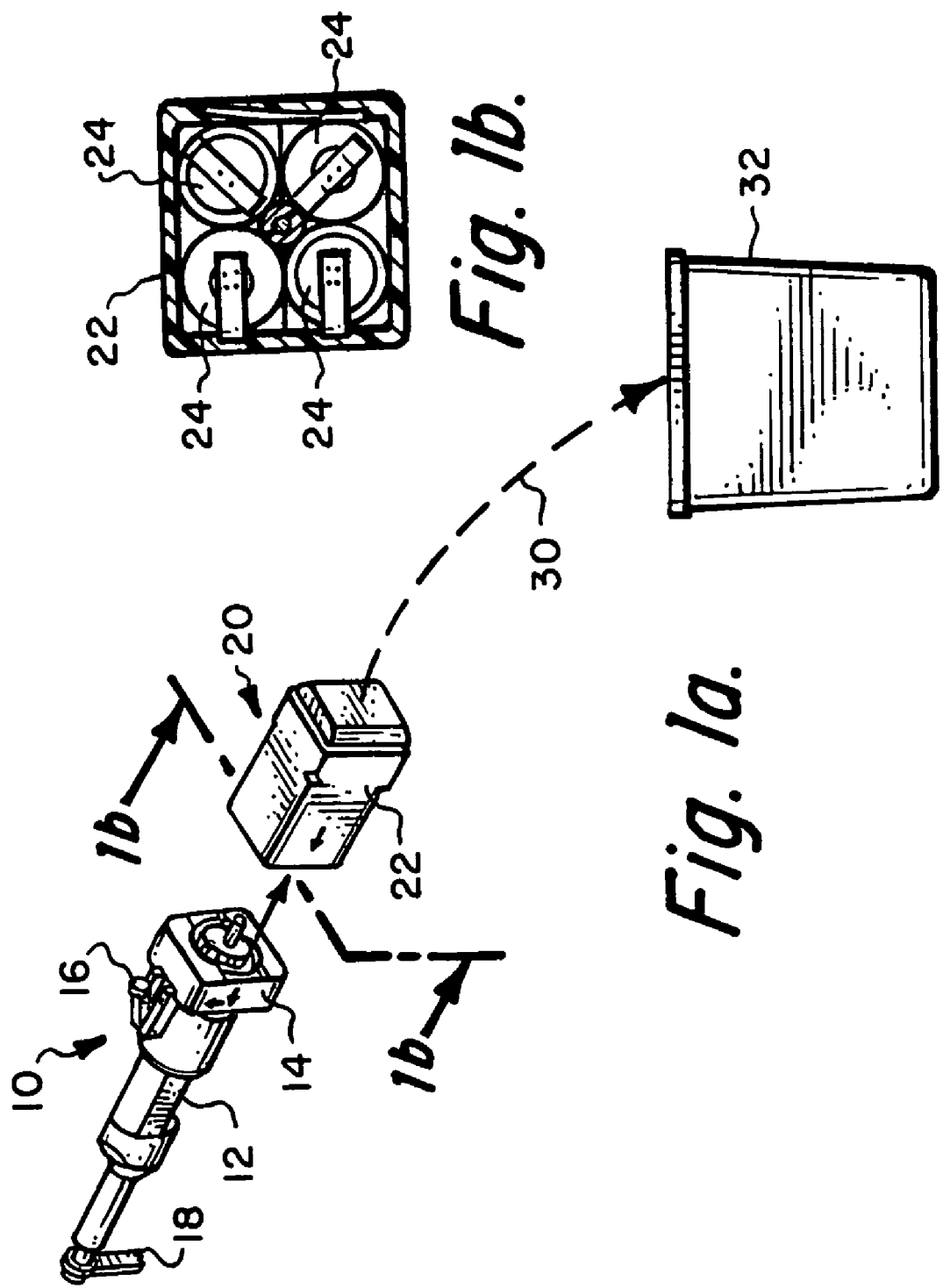

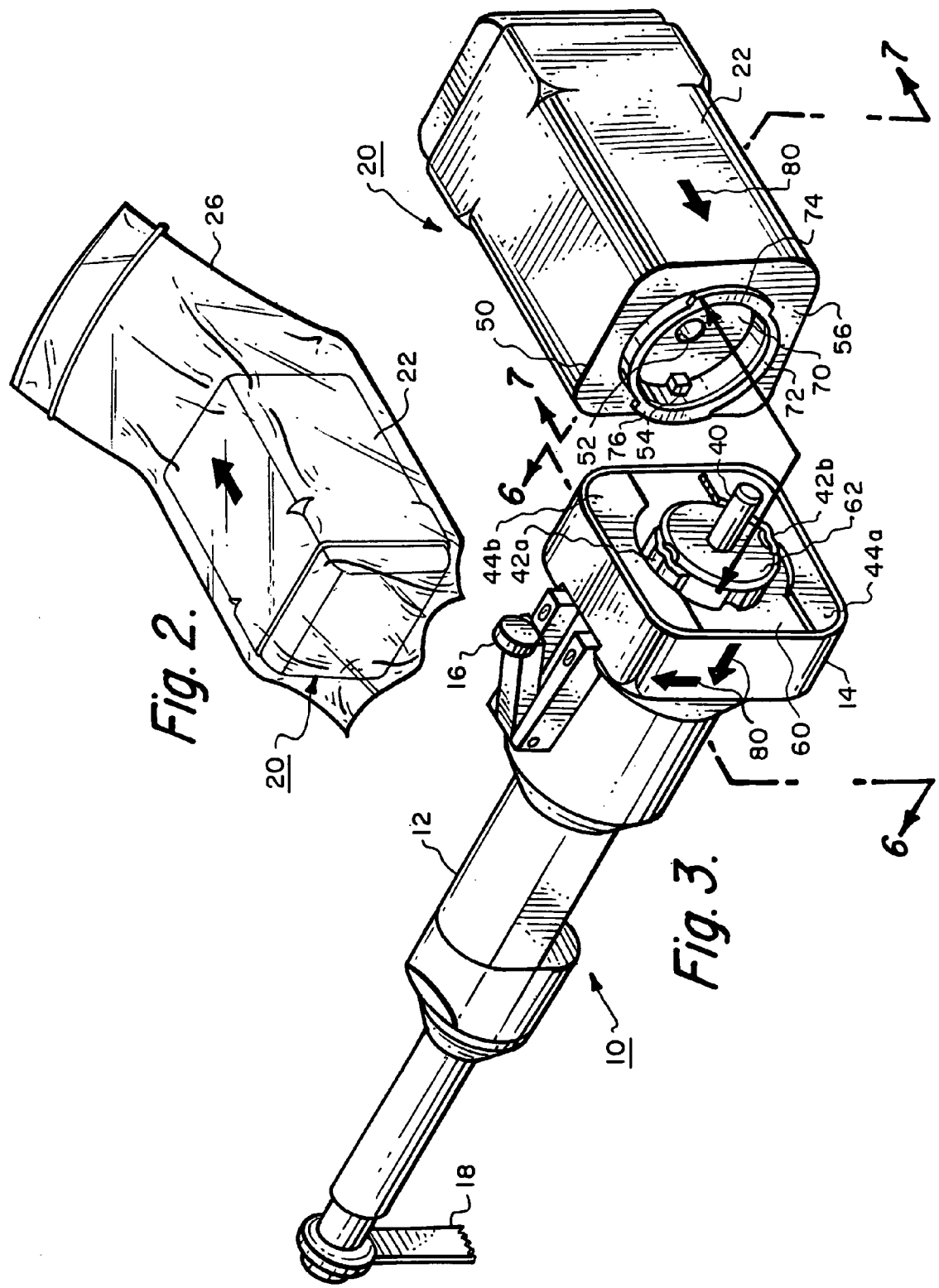

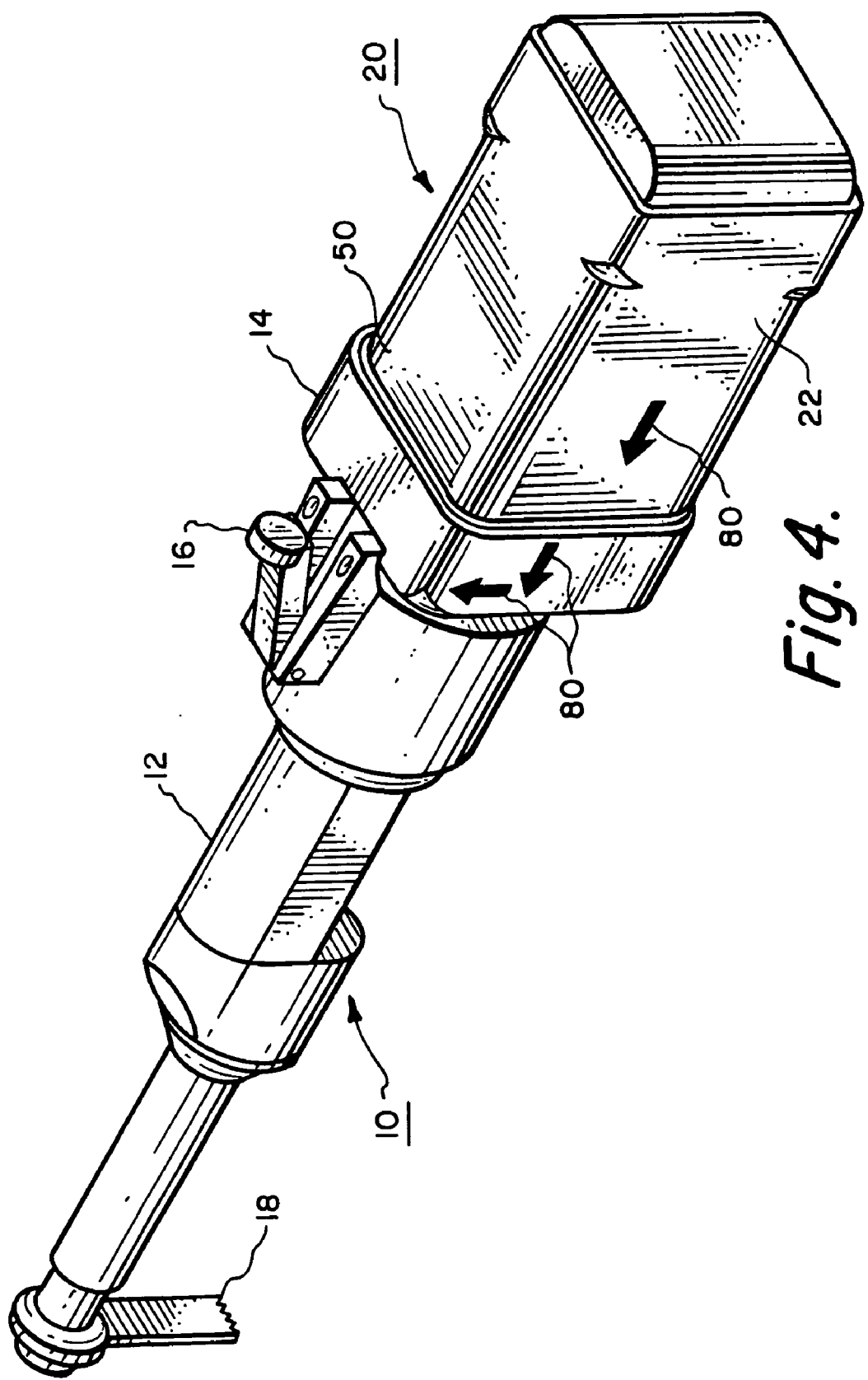

CORDLESS SURGICAL HANDPIECE WITH DISPOSABLE BATTERY; AND METHOD

PRIORITY CLAIM

This application claims the benefit of our application Ser. No. 09/349,643 filed Jul. 8, 1999 now U.S. Pat. No. 6,126,670 and of our Provisional Application 60/112,678 filed Dec. 16, 1998.

FIELD OF THE INVENTION

The present invention relates to electrically operated surgical tools and methods of their use.

BACKGROUND OF THE INVENTION

An important economic factor for any surgical tool or machine is the amount of unproductive time spent in its operation. This comes in the form of training and initial set-up. Before a surgical procedure begins, the users need to know how to operate the instrument and be familiar with all its controls. Hospital personnel must set up the instrument system before it can be used. This involves connecting all the power lines, calibration, and verifying function. Both user's training and instrument system set-up entail time and cost by the medical facility.

The most unique aspect of surgical equipment is the need for sterility. To prevent infections and to aid healing, surgical equipment is sterilized. The effort this takes and the success with which it occurs varies depending on the equipment. The maintenance of sterility in the surgical site is a major factor in health care. Non-sterile or partially sterile instruments may be considered to harbor bacteria or toxic debris. Each of these will lead to an inflammatory response from the body and associated infection, carcinogenosis and cell necrosis. Contamination will lead to grave systemic effects on the patients of orthopedic surgery, which by its nature is highly invasive. The maintenance of a sterile operating field is of prime importance in surgical handpieces.

Corded Instrument Systems

The use of a corded instrument system dictates that only one handpiece may be used at any one time per console. When another instrument is needed the console cord must be switched to another instrument. Procedures where it is imperative that two instruments be used simultaneously necessitate two consoles. Handpiece instrument consoles are expensive and the need for duplication is a distinct disadvantage. Disconnecting and reconnecting instruments to the console cord takes a certain amount of work and time. Using cordless instruments reduces instrument transfer time.

A reusable cord must be properly sterilized prior to surgery in an expensive and complex in-house sterilizer. Once sterile, the cord must be carefully transported to the operating room. There the cord becomes partially non-sterile due to its console connection.

When a corded handpiece is transferred and exchanged to other medical personnel, the cord must be handled. However, there is no way to tell which part of cord has fallen out of the sterile field. This poses an increased risk of contamination to the user and the surgical site.

When multiple handpieces are exchanged they are extensively handled. This is because the cord must be disconnected and reconnected to each handpiece. Handling increases the risk of contamination. This risk is greatly minimized with cordless instruments.

Following a surgical procedure, the instrument cord needs to be thoroughly cleaned prior to its next use. This involves cleaning blood and tissue off the cord with powerful solvents and cleaners. These agents attack the cord and limit its useful life. The cord must be handled by trained medical personnel. A disposable power pack would eliminate these extra tasks and their associated costs.

Cordless Instruments

During a surgical procedure it is often necessary to use more than one handpiece. Saws and high speed handpieces are used for cutting, shaping and in general removing portions of bone. Drills are used primarily for making holes, which are then used for inserting wires, pins or screws. These two operations are often used in conjunction with one another during bone and tissue repair procedures. Current pencil grip surgical instruments make it difficult to use more than one instrument at a time during a surgical procedure.

A cordless handpiece is easier for the physician to operate than similar corded handpieces. The controls are basic and are controlled with one hand. Equivalent corded handpieces require complex console instructions and commands.

A further advantage of cordless handpieces is the greater ease of set-up. Equipment set-up is a significant time issue for hospitals. Corded systems have complicated and time-consuming assembly procedures. Multiple connections are involved. A user must be trained at setting up and operating the console system.

In instances where a powered surgical instrument is needed immediately, a cordless instrument can be immediately transported to that area. This is true regardless of the surrounding environment. That is not true of a corded unit.

A surgical instrument cord, connected to a non-sterile console, may be considered only partially sterile. This by itself compromises the integrity of a surgical site. A cordless handpiece maintains sterility throughout the entire surgical operation.

Surgical procedures often involve cuts at more than one position at a surgical site. A convenient way to accomplish this is to pass the surgical instrument over the surgical site. With a corded instrument, this would unfortunately result in the cord being passed over, and perhaps falling into, the surgical site. The resulting tissue damage and contamination can have grave consequences. A cordless instrument can easily be passed over the surgical site without contamination risks. Likewise, a physician who needs to make multiple cuts or holes at various surgical locations needs to be in the position that best suited him or her without trailing a bulky, cumbersome partially sterile cord.

Cordless instruments have heretofore utilized batteries of the rechargeable type. This adds special problems, because the battery must be sterilized before use; and after each use it must be recharged and then sterilized in preparation for the next use. Presently available batteries do not lend themselves well to this process.

SUMMARY OF THE INVENTION

According to the present invention a method of performing surgery is provided, in which bone or hard tissue may be cut, shaped, or drilled by means of a cordless powered surgical instrument, but without the necessity of subsequently recharging a battery or re-establishing its sterile condition.

According to the invention a disposable battery pack can be easily connected to a surgical instrument, both electrically and mechanically, and after a single use may be detached and safely disposed of as non-hazardous waste, into the waste system.

Further according to the invention a method of performing a surgical procedure is disclosed, utilizing a cordless surgical handpiece powered from a sterile battery pack in which the battery chemistry is based upon lithium/manganese dioxide, the battery being in condition for immediate use without further charging or sterilization, and being adapted after a single use to be disposed of into non-hazardous waste.

Still further according to the present invention a surgical handpiece and disposable battery are provided with mating sets of electrical contacts which can be mechanically and conductively locked together to ensure correct alignment of the parts, as well as stable mechanical support and reliable electrical operation of the handpiece during the surgical procedure.

According to yet another feature of the presently preferred form of the invention, a surgical handpiece and a disposable battery each has a defined longitudinal axis with a set of electrical contact elements arranged generally concentric to that axis, and when those parts are aligned on a mutual longitudinal axis the sets of contacts are adapted to become lockingly and conductively interengaged in response to rotation of the battery pack relative to the handpiece.

Still another feature of the invention is that when using a compact surgical handpiece with a brushless DC motor and a manually operated external trigger for activating and controlling the motor operations, a compatible disposable battery may also be used, with interengaging sets of contacts on the handpiece and battery adapted to become lockingly and conductively interengaged upon rotation of the battery pack relative to the handpiece in a manner that rapidly achieves correct alignment of the parts and also ensures stable mechanical attachment and support during the surgical procedure.

DRAWING SUMMARY

FIG. 1(a) is a schematic view of a surgical handpiece in accordance with the invention, showing disposal of an associated battery pack into non-hazardous waste after it has been used;

FIG. 1(b) is a cross-section view taken on the Line 1(b)—(1(b) of FIG. 1(a), showing that the battery pack when being disposed of still contains batteries;

FIG. 2 is a perspective view of a sterile battery pack in its plastic container, in accordance with the invention;

FIG. 3 is an exploded perspective view of the handpiece and battery pack before they are assembled together;

FIG. 4 is a perspective view of the instrument assembly during attachment of the battery pack, with arrows indicating the direction of movement of the battery pack;

DETAILED DESCRIPTION

Figure 5:
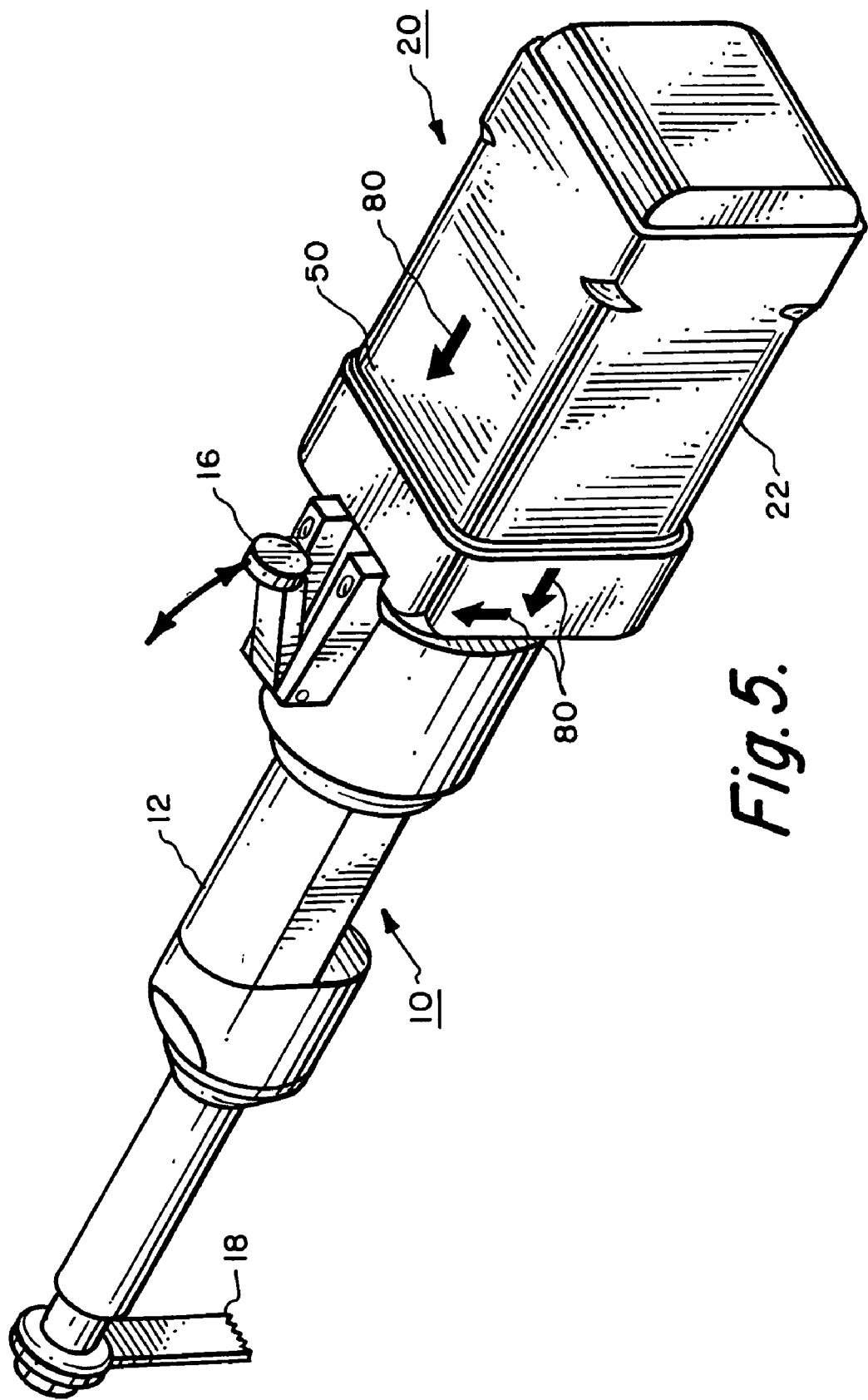
FIG. 5 is a perspective view of the instrument assembly after attachment of the battery pack, with arrows showing that the battery pack has been rotated by ninety degrees.
Figure 6:
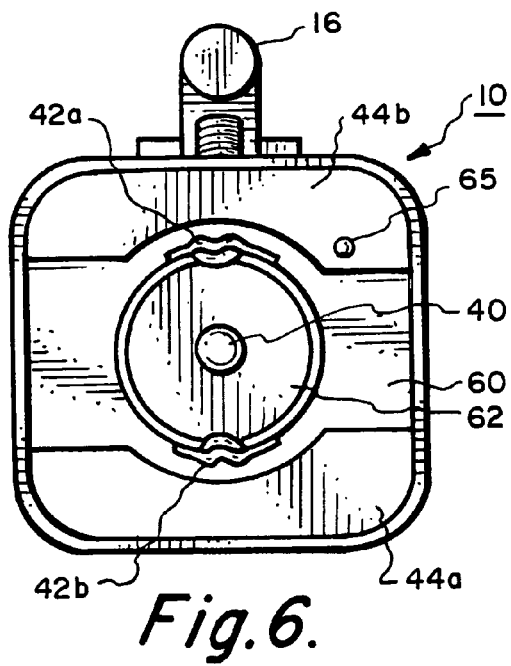
FIG. 6 is a rear end view of a surgical drill or handpiece in accordance with the invention taken along line 6—6 of FIG. 3.
Figure 7:
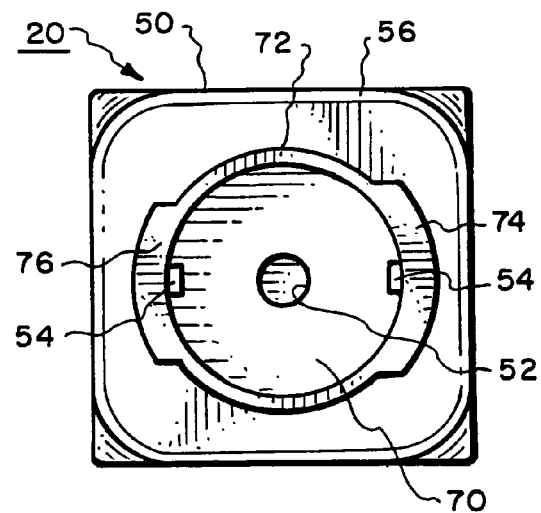
FIG. 7 is a front end view taken along line 7—7 of FIG. 3 of the disposable battery pack.

In FIGS. 1(a) and 1(b) a surgical handpiece 10 with housing 12 has a rearward or base end 14, an externally mounted trigger 16, and a tool 18 on its forward end. A disposable battery pack 20 has a housing 22 and contains internal batteries 24. Arrow 30 indicates the disposal of battery pack into a waste basket 32 after the surgical handpiece has been used in a surgical procedure.

As is conventional, the surgical handpiece is a compact device containing a brushless DC motor for moving the tool member 18, a manually operated trigger 16 used for activating motor control operations, and an adjustable tool support mechanism for orienting the tool 18 and securing it in place. An electronic circuit, not specifically shown, controls and regulates the energy supply to the motor, and is operated externally by the trigger 16. Trigger 16 may also control the range of speed, the direction of the cutting tool, and cutting tool braking.

According to the present invention the energy supply for the handpiece is provided by the battery pack 20 which is secured onto the handpiece by means of a rotating movement. This detachable DC electric energy supply ensures correct orientation of the electrical contacts in the battery to those for the handpiece, and also signals to the operator by sound, sight, and touch that the battery is correctly secured in place.

The battery pack 20 is pre-sterilized and packaged for immediate use in a surgical environment. FIG. 2 shows a plastic cover 26 which is preferably used to enclose the battery pack prior to its use. The battery pack 20 consists of primary batteries 24 which by definition do not require charging before use. These batteries retain their initial charge for long periods of time. The battery pack is discarded after use and may be considered a disposable component of the instrument system.

Further according to the invention the battery pack preferably contains primary batteries 24 whose chemistry is based upon lithium/manganese dioxide, such as the DL 2/3A manufactured by Duracell, Inc. of Bethel, Conn. These batteries possess a high energy density, have a high rate capability over a broad temperature range, and have excellent capacity retention.

As shown in FIG. 3 the handpiece 10 at its rearward or battery receiving end 14 has an alignment post 40 extending therefrom, which defines a longitudinal axis of the handpiece. It also has a set of electrical contact elements 42a and 42b which are concentric to that axis. The sterile and disposable battery pack 20 has an attachment end 50 with a central opening 52 therein, the opening 52 also defining a longitudinal axis of the battery pack. The battery pack 20 also has a set of electrical contact elements 54 which are concentric to its longitudinal axis. The central opening 52 in the disposable battery pack 20 is adapted to insertably receive the alignment post 40 so as to establish a mutual alignment axis of the handpiece 10 and battery pack 20.

The battery receiving end of the handpiece 10 also has flat end surface surfaces 44a and 44b which are adapted to be engaged by the battery pack. The forward or attachment end of the disposable battery pack has a flat end surface 56 adapted for abutting engagement with the end surfaces 44a and 44b while yet allowing relative rotation of the battery pack relative to the handpiece.

The set of contacts 42a and 42b on the battery receiving end of the handpiece and the set of contacts 54 on the attachment end of the disposable battery pack are mating sets of electrical contact elements, each set being arranged generally concentric to the mutual alignment axis. Upon the insertion of the alignment post 40 of the handpiece into the opening 52 of the battery pack, the sets of mating contacts are adapted to then become lockingly and conductively interengaged in response to rotation of the battery pack relative to the handpiece.

In operation, the post 40 is first partially inserted into opening 52 to establish alignment of battery and handpiece. Then with further insertion, the two sets of contacts will assume a position in concentric relation to their common mutual axis of alignment.

The Interlocking Parts

Referring now to FIGS. 3, 6, 8, 9, and 12, the detailed structure of the rearward end of handpiece 12 is shown. Rearward end 14 of the housing of handpiece 12 has an aluminum cover. An end plate 60 made of aluminum closes the rearward end of handpiece housing, as best seen in the cross-section views of FIGS. 8 and 9. End plate 60 is recessed inwardly from the extreme rearward end of the housing.

There are a pair of electrical contacts 42a and 42b which protrude out from end plate 60. Those contacts do not support themselves, however; a plastic cylinder 62 is secured to end plate 60, and the contacts 42a 42b, are secured to the outer wall of plastic cylinder 62, about 180 degrees apart. One contact is of course positive, and the other negative.

Figure 8:
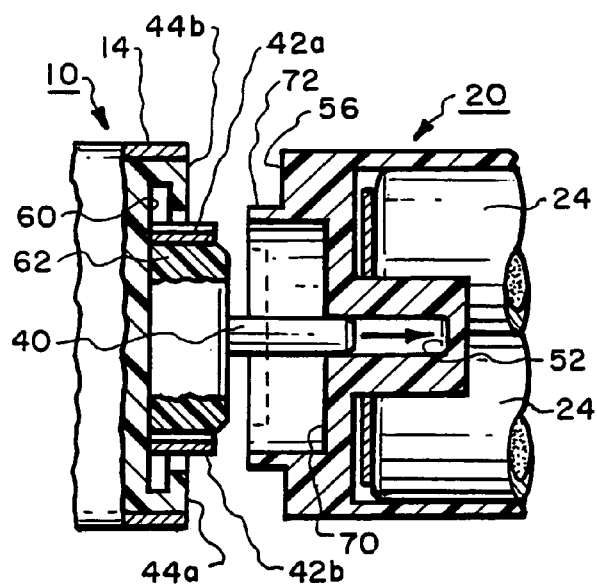
FIG. 8 is a longitudinal cross-sectional view showing initial alignment of the battery pack to the surgical drill.
Figure 9:
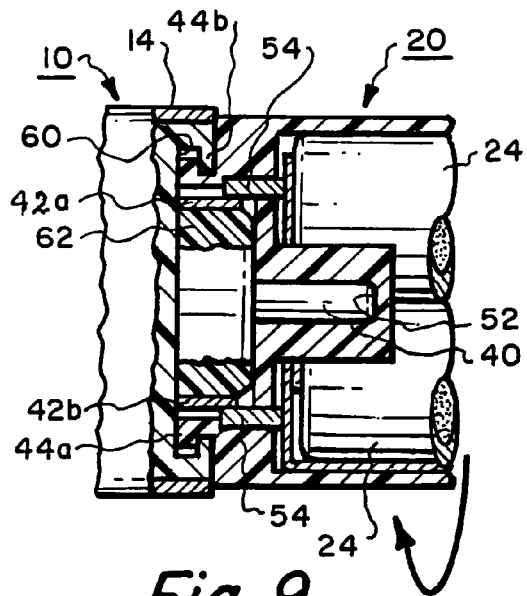
FIG. 9 is a cross-sectional view like FIG. 8, but showing the battery pack after its full insertion and its rotation into a locking attachment.
Figure 10:
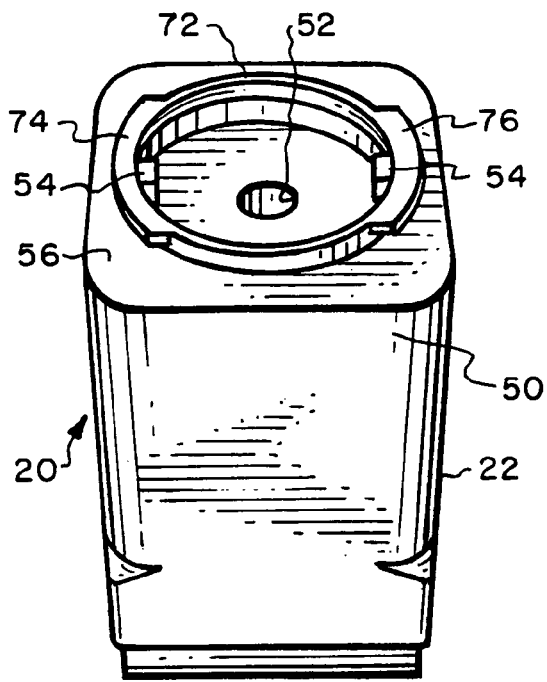
FIG. 10 is a perspective view of the battery pack showing in detail its forward end.
Figure 11:
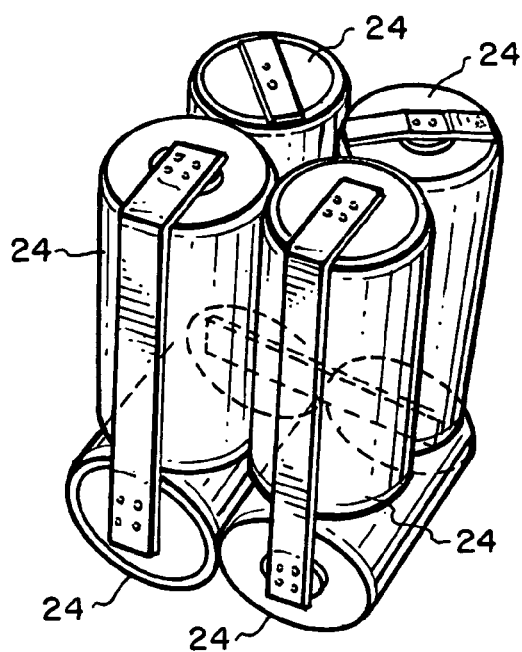
FIG. 11 is a perspective view of the batteries contained within the battery pack.
Figure 12:
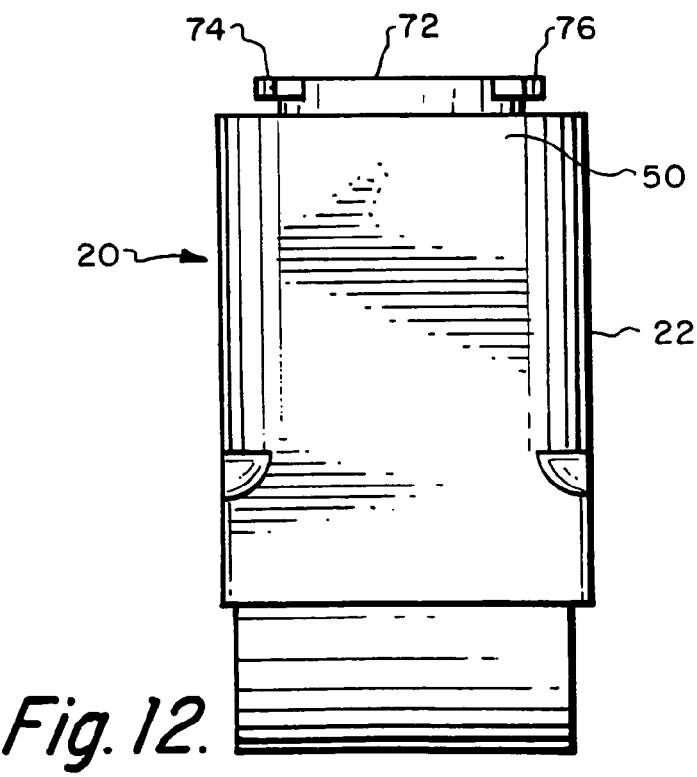
FIG. 12 is a side elevation view of the battery pack.

The rearward end of the handpiece also has flanges that are part of and protrude outward from end plate 60 to control the insertion and locking of the battery pack, designated on FIG. 3 by numerals 44a and 44b. On the left side as seen in FIG. 3, there is a wide gap between 44a and 44b. On the right side as seen in FIG. 3, there is a narrow gap. The flanges are preferably formed as an integral part of the end plate 60, as shown in FIG. 8. A stop pin 65 seen in the upper right portion of FIG. 6 protrudes inwardly behind flange 44b and limits the rotation of the battery contacts relative to the handpiece.

The front end of battery pack 20 is shown in FIGS. 3, 7, 8, 9, and 10. It has a front end plate 70, formed of plastic material, such as ABS plastic; see FIG. 8. End plate 70 also has a projecting ring 72, with flanges 74, 76. As best seen in FIG. 3, flange 74 on the near side of the battery pack will fit into the gap between lower flange 44a and upper flange 44b of the handpiece, which gap is also on the left as seen in FIG. 3.

The other flange 76 on far side of battery pack will fit between flanges 44a, 44b on the far or right side of the handpiece as seen in FIG. 3. However, flange 74 is too wide to enter the gap on the right side as seen in FIG. 3. Therefore, battery pack 20 must be engaged with the handpiece in a predetermined relative position.

FIG. 8 shows alignment of the two parts of apparatus on their mutual longitudinal axis as the post 40 makes its initial entry into the center hole 52 of the battery pack. Further insertion of the post ensures the coaxial alignment of the two parts.

Rotating the Battery Pack to Locked Position

Then battery pack 20 is rotated to the right, as indicated by arrows 80 in FIGS. 3, 4, and 5. FIG. 5 shows the locked position, also shown in more detail in FIG. 9. Further rotation of the battery pack relative to the handpiece is prevented by the stop pin 65. The contact elements 42a and 42b are made as spring members, so that when the contact elements 54 of the battery pack are seated, there is an audible noise to tell the operator that the properly aligned operating position has been reached. Thus the apparatus includes means providing a spring-supported snap action so that the sets of mating contacts become lockingly and conductively interengaged in response to rotation of the battery pack relative to the handpiece.

It will also be noted that the battery receiving end of the handpiece, and the attachment end of the battery pack, each has a non-circular external cross-sectional configuration. Thus in the presently preferred embodiment of the invention the two housings are essentially square with rounded corners. The two external configurations are closely similar in both size and shape, and the rotational position of the battery pack when the contacts are locked together is such that the handpiece and the battery pack then provide an essentially continuous external surface. This indicates to the hand of the operator that correct alignment of the contacts has been achieved.

Advantages of Cordless Surgical Handpieces

Orthopedic surgical instruments are widely used in many delicate bone working procedures. These include spinal surgeries, neurosurgeries and other bone sculpting operations. For these surgeries, a small, light weight, well balanced instrument is desired. The handpiece needs to have high speed and power, and be sterilizable.

The ergonomics of a pencil grip cordless instrument is quantifiably better than corded or pistol grip handpieces. Pencil grip allows more, fine motor control and easier eye-hand coordination. The improved ergonomics of the pencil grip results in less fatigue by the user.

A cordless handpiece is more mobile than a corded unit. This makes it easier to pass it around the surgical site, from physician to attendant or assistant. A cordless system is also not weighed down by a cord. The back of corded or pistol grip handpieces can require tugging or lifting of the handpiece cutting tool, which makes cutting more difficult. The cord diameter is very thick for a high performance system, which again limits mobility.

A further disadvantage of a corded instrument is that it is tethered. The handpiece can only be operated at a given distance from the console, restricted by the length of the cord. The cord also has associated inductance and capacitance properties which can affect the handpiece performance or electrical complexity of the system.

For movement about the surgical site with a corded handpiece, extra cord is needed. The extra cord is either coiled by the physician, held by an attendant or attached to a surgical stand. This coiling necessitates extra labor by operating room (OR) personnel, takes up critical surgical site space and limits mobility of other OR personnel.

The mobility and transport of cordless, pencil grip instruments is of particular advantage when multiple instruments are needed in a procedure. This is often the case where drilling, sawing and wire driving are all needed. These often come in rapid succession and in different sequences. Time is a critical factor for successful surgical outcomes.

Electrical Advantages of Cordless Instruments

Instrument performance is of critical importance in surgical procedures. A key electrical factor with corded handpieces is the cord itself. The power cord has a given length associated with it and electrical properties of its own.

The internal impedance of the cord increases electrical losses and reduces power and performance. The power is lost as heat and many have other electro-magnetic interference (EMI) problems associated with it. The length of cord and flexibility needed usually necessitate the use of three-phase current.

The cord also has associated inductance and capacitance properties which reduces performance and necessitates more complex electronics in the console. There are also associated EMI problems with this inductance and impedance. These factors exist with both DC and, especially, AC signals.

The electrical properties of the cord are directly proportional to its length and can only be minimized by shortening the cord or making it thicker. A shorter cord reduces mobility. A thicker cord reduces flexibility and increases costs.

The EMI problems associated with a cord occur along the entire cord length. The two connections are especially prone to emissions. Cordless instruments, on the other hand, run on direct current (DC), have only one connection point and minimized electronics. The basic level of emitted EMI from the battery to handpiece connection, in a cordless handpiece, is zero.

A corded surgical instrument has a direct connection between the patient and wall or line voltage. Power surges from the outlet must be properly controlled before they reach the patient. A cordless instrument which operates with lower voltage, less energy, and a limited capacity power supply, poses a much lower electrical threat to the patient.

The calibration and preventive maintenance costs associated with a corded handpiece console are not a factor with a cordless system. The elimination of the console results in more operating room table space. This valuable space can then be used for important instruments and equipment which need to be close at hand.

Cost and Reliability of Cordless Systems

The cost and reliability of any surgical instrument is of critical importance. OR expenses are high and are based on time usage. All general surgeries have a time factor based on how long the room is occupied and the patient is under anesthesia. Instrument systems must properly work or the operation's success, and thus the patient's health, will be affected.

Cord breakage or damage is a prevalent problem and necessitates cord replacement or repair. Cord failure may also damage the handpiece and/or console through electrical shorts or otherwise. Even partial failure will directly decrease the performance of the surgical system. Cord repair and replacement is expensive, as is system repair and replacement.

Due to the high failure rate of cords, as well as their importance to the handpiece system, they must be tested often. This results in time and expense to the medical facility, even when they are functional.

Cord damage may result in heat build-up or exposed electrical leads. These pose serious risks to the operators as well as the patient.

Sterilization and cleaning using hospital grade detergents have serious negative effects on the cord. These thermal and chemical agents directly reduce the life of the cord, as well as increase the likelihood of damage.

Cord damage may also result in improper system communications and linkage. This may result in increased cord impedance and consequent loss of handpiece performance. Improper signaling may also lead to improper motor operations and result in handpiece overheating. This may be a hazard to either the user, patient or attending personnel.

Advantages of Disposable Battery Packs

The high operating costs of surgical arenas and medical personnel dictate the use of low maintenance, easy to use equipment. Many times this means single use or disposable components. Also supporting disposable product use is the issue of sterility and contaminants from the surgical site. Surgical equipment is often made disposable whenever possible. Packaged pre-sterile, disposable medical equipment, by its nature, is easy to use and maintain and often very cost-effective.

Disposable, primary battery packs offer a higher energy capacity per volume than equivalent rechargeable batteries. The batteries are smaller, which is a distinct advantage in cordless surgical handpieces.

Disposable, primary battery packs offer a higher energy capacity per weight than equivalent rechargeable batteries. The batteries are lighter, which is a distinct advantage in cordless surgical handpieces.

Disposable batteries are inspected at the manufacturer by trained personnel prior to each use. This gives the products a higher reliability per use than equivalent reusable batteries. This is an advantage during critical use situations that often occur in the operating room.

Every battery pack has full running power immediately upon attachment. Rechargeable batteries, on the other hand, must be tested to verify their immediate charge capacity.

Due to the nature of disposable batteries there is no pre- or post operation clean-up involved. This reduces the amount of time hospital personnel need to service the equipment.

Reusable batteries will exhibit wear after repeated use. This results in debris build-up on components, particularly oxidation on electrical contacts, weakening of the housing and general degradation. This may result in poor or unacceptable product performance. Disposable products do not have these associated problems.

Disposable, primary batteries may be entered into the normal waste stream. Standard rechargeable batteries are considered toxic and must be properly disposed of outside the normal waste stream.

Most disposable primary batteries may be transported by air or other standard methods. Some types of rechargeable batteries need special handling conditions and permits to be safely transported.

By their very nature disposable primary battery cells have an immediate charge capacity, unlike rechargeable battery cells. Rechargeable batteries need to be charged on specialized and dedicated chargers. This is an expensive and bulky piece of equipment for the medical facility.

Rechargeable, secondary batteries need to be recharged immediately prior to each use because they lose their electrical charge very quickly. Primary batteries retain their charge for very long periods of time, over ten years. This results in lower service and maintenance costs to hospital for disposable batteries.

Primary batteries have a much lower cost base than equivalent rechargeable batteries. This usually has the advantage of saving money for medical facilities.

Disposable primary cells generally have a higher voltage, and thus a higher energy potential than rechargeable cells. Furthermore, a higher voltage allows most standard electrical and electromechanical components and motors to operate more efficiently, with fewer components, at a lower cost.

Disposable, primary batteries retain their charge capacity under more varied conditions, including thermal, humidity and mechanical (e.g. vibration or shock) than equivalent rechargeable battery cells. This increased robustness is an advantage in surgical operations.

In improper use conditions, such as a short circuit, many types of batteries will vent their internal electrolyte in the form of a gas. If, due to improper conditions, primary batteries vent internal gas, these gases are non-toxic. This is unlike some types of rechargeable batteries. That can be a critical issue in an operating room where it would be very difficult to evacuate the area if this condition arose.

Alternate Embodiment

Figure 13:
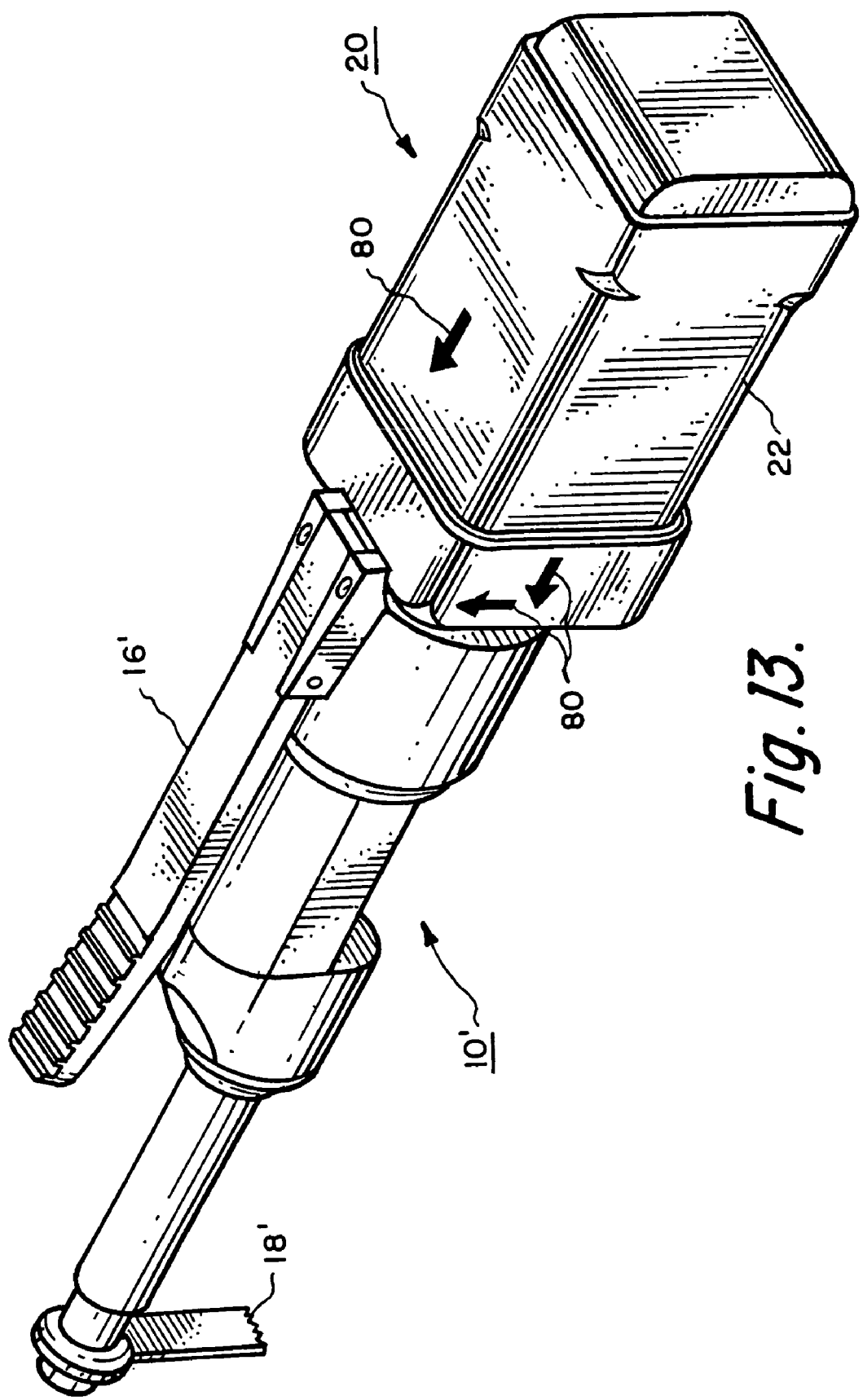
FIG. 13 is a perspective view of a complete instrument showing an alternate form of trigger for handpiece control.

In the alternate embodiment of the present invention as shown in FIG. 13, the handpiece 10' has a rather long-handled trigger 16'.

While the presently preferred embodiment of the invention has been disclosed in detail in order to comply with requirements of the patent laws, it will be understood by those skilled in the art that some variations may be possible within the concept of the invention. It will therefore be understood that the scope of the invention is to be determined only in accordance with the appended claims.

What we claim is:

1. A surgical instrument comprising:
   (a) a handpiece having a tool supporting end, and a battery receiving end, the battery receiving end having:
       a first set of substantially concentrically arranged electrical contacts; and
       first and second opposing flanges substantially perpendicular to and opposing a longitudinal axis of the handpiece and separated by first and second gaps of substantially different widths opposing the longitudinal axis; and
   (b) a sterile package comprising a single surgical use, disposable battery pack having an attachment end, the attachment end having;
       a second set of substantially concentrically arranged electrical contacts; and
       third and fourth flanges opposing the handpiece longitudinal axis, substantially parallel to and slidably engaged with the first and second opposing flanges, and configured to pass through a corresponding one of the first and second gaps in a single, predetermined relative position;
   (c) wherein the two sets of contacts are adapted to become lockingly and conductively interengaged upon engagement of each of the third and fourth flanges with a corresponding one of the first and second flanges in response to rotation of the battery pack relative to the handpiece.

2. A surgical instrument as in claim 1 wherein the battery pack has chemistry based upon lithium/manganese dioxide, the battery pack after use being disposable into non-hazardous waste.

3. The surgical instrument as in claim 1 further comprising a surgical tool coupled to the tool supporting end and configured for performing a cutting operation on live human bone or hard tissue.

4. The surgical instrument as in claim 1 further comprising a surgical tool coupled to the tool supporting end and configured for performing a drilling operation on live human bone or hard tissue.

5. The surgical instrument as in claim 1 further comprising a surgical tool coupled to the tool supporting end and configured for performing a shaping operation on live human bone or hard tissue.

6. A surgical instrument for performing a cutting, shaping, or drilling operation on live human bone or hard tissue, comprising:
   (a) a handpiece having a battery receiving end with an alignment post extending therefrom and a tool supporting end for supporting a tool for performing a cutting, shaping, or drilling operation on live human bone or hard tissue; and
   (b) a sterile package containing a single use, disposable battery pack which has an attachment end with a central opening therein;
   (c) the central opening in the single use, disposable battery pack being adapted to insertably receive the alignment post so as to establish a mutual alignment axis of handpiece and battery pack;
   (d) the battery receiving end of the handpiece and the attachment end of the single use, disposable battery pack having flat end surfaces adapted for abutting engagement while yet allowing relative rotation of the battery pack relative to the handpiece;
   (e) the battery receiving end of the handpiece and the attachment end of the single use, disposable battery pack having mating sets of electrical contact elements, each set being arranged generally concentric to the mutual alignment axis; and
   (f) wherein upon the insertion of the alignment post of the handpiece into the opening of the battery pack, the sets of mating contacts are adapted to then become lockingly and conductively interengaged in response to rotation of the battery pack relative to the handpiece.

7. The apparatus of claim 6 wherein the chemistry of the disposable battery pack is based upon lithium/manganese dioxide.

8. The apparatus of claim 6 including means providing a spring-supported snap action whereby the sets of mating contacts become lockingly and conductively interengaged in response to rotation of the battery pack relative to the handpiece.

9. The apparatus of claim 8 wherein the spring-supported snap action means provides an audible sound indicating that the mating contacts and the battery have been correctly and securely locked in position.

10. The apparatus of claim 6 wherein the battery receiving end of the handpiece, and the attachment end of the battery pack, each has a non-circular external cross-sectional configuration, the two external configurations being closely similar in both size and shape, and the rotational position of the battery pack for locking the contacts being such that the handpiece and the battery pack then provide an essentially continuous external surface which indicates to the hand of the operator that correct alignment of the contacts has been achieved.

11. The apparatus of claim 10 including means providing a spring-support snap action whereby the sets of mating contacts become lockingly and conductively interengaged in response to rotation of the battery pack relative to the handpiece.

12. A surgical instrument for performing a surgical drilling procedure on bone or hard tissue, comprising:
 (a) a handpiece having a rotary driven drilling member supported by a tool supporting end, and a battery receiving end with an alignment post extending therefrom, the battery receiving end of the handpiece also having a set of electrical contact elements arranged in generally concentric relation to the alignment post;
 (b) a disposable battery having an attachment end with a central opening therein, and a set of mating electrical contact elements arranged in a generally circular configuration concentric to the central opening therein;
 (c) the central opening in the disposable battery being adapted to receive the alignment post of the handpiece in a partially inserted position so as to establish a pre-attachment alignment thereof;
 (d) the sets of mating contacts being adapted to come into a mutually concentric relation in response to a further insertion of the alignment post into the central opening; and
 (e) the sets of contacts being adapted to then become lockingly and conductively interengaged upon rotation of the battery pack relative to the handpiece.

13. The apparatus of claim 12 wherein the chemistry of the disposable battery is based upon lithium/manganese dioxide, and which further includes a sterile package containing the disposable battery.

14. A surgical instrument for removing live human bone or hard tissue, comprising:
 a handpiece including:
  a first end supporting a rotary driven tool configured to remove live human bone or hard tissue by rotation of a cutting member in response to rotary drive means within the handpiece; and
  a second end having:
   an alignment post extending therefrom and defining a handpiece longitudinal axis; and
   a plurality of handpiece electrical contacts arranged concentric to the handpiece longitudinal axis; and
 a sterile, disposable battery pack including:
  lithium/manganese dioxide batteries; and
  an attachment end configured to be secured to the handpiece second end by means of a rotating movement of the disposable battery pack relative to the handpiece, the attachment end having:
   an opening therein defining a battery pack longitudinal axis; and
   a plurality of battery pack electrical contacts arranged concentric to the battery pack longitudinal axis; wherein
 the attachment end opening is configured to receive the handpiece alignment post so as to establish a mutual alignment axis between the handpiece longitudinal axis and the battery pack longitudinal axis; and
 the pluralities of the handpiece and battery pack contacts are mating pluralities of contacts configured to be lockingly and conductively interengaged in response to the rotating movement.

15. The surgical instrument of claim 14 wherein the handpiece and the disposable battery pack each have a substantially non-circular external cross-sectional configuration and provide a substantially continuous external surface when the pluralities of handpiece and battery pack contacts are lockingly and conductively interengaged.

16. The surgical instrument of claim 14 wherein the handpiece second end includes first flat end surfaces and the disposable battery pack includes second flat end surfaces configured for abutting engagement with the first flat end surfaces while allowing rotation of the battery pack relative to the handpiece.

* * * * *